(12) United States Patent
Howell et al.

(10) Patent No.: US 6,344,324 B2
(45) Date of Patent: Feb. 5, 2002

(54) QUANTIFICATION OF CELLULAR INJURY USING EXPRESSION OF A FLUORESCENT PROTEIN UNDER THE CONTROL OF THE GADD153 PROMOTER

(75) Inventors: Stephen B. Howell, Del Mar; Xinjian Lin; Dennis P. Gately, both of San Diego, all of CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/479,529

(22) Filed: Jan. 7, 2000

(51) Int. Cl.$^7$ .................................................. C12Q 1/68
(52) U.S. Cl. .............................. 435/6; 435/29; 435/366; 435/371
(58) Field of Search ........................... 424/93.21, 277.1; 435/410; 530/350; 800/3, 5

(56) References Cited

PUBLICATIONS

Ramiro et al. Enhanced green fluorescent protein as an efficient reporter gene for retroviral transduction of human multipotent lymphoid precursors. Human gene therapy. vol. 9, 1103–1109, 1998.*

Luethy et al. Activation of the gadd 153 promoter by genotoxic agents: A rapid and specific response to DNA damage. Cancer Research. vol. 52, pp. 5–10, 1992.*

* cited by examiner

Primary Examiner—Deborah Crouch
(74) Attorney, Agent, or Firm—Benjamin Aaron Adler (57) ABSTRACT

The present invention features a novel cellular injury reporter system in which a chimeric gene containing the GADD153 promoter linked to the coding region of an enhanced green fluorescent protein (EGFP) gene was stably integrated into the genome of carcinoma cells. Activation of the GADD153 promoter was quantified using flow cytometric measurement of EGFP expression following drug exposure. This reporter system is suitable for high. throughput in vitro and in vivo screening for agents capable of producing cytotoxicity via a wide variety of different mechanisms, and can be utilized to investigate the relative potency of structurally related DNA adducts.

8 Claims, 5 Drawing Sheets

QUANTIFICATION OF CELLULAR INJURY USING EXPRESSION OF A FLUORESCENT PROTEIN UNDER THE CONTROL OF THE GADD153 PROMOTER

BACKGROUND OF THE INVENTION

1. Field of the Invention

The present invention relates generally to the fields of molecular biology and toxicology. More specifically, the present invention relates to a molecularly engineered cell line that functions as a reporter system for the detection of cellular injury.

2. Description of the Related Art

Exposure of cells to genotoxic agents results in the induction of a number of damage response genes. In bacteria, damage to DNA or inhibition of its replication invokes the well-characterized SOS response with the induction of approximately 20 different genes (1). In yeast, an even larger number of genes are involved in the cellular injury response, and the identity of some of those responsible for executing cell cycle arrest and detecting and repairing DNA damage are now known (2,3). Thus, it is not surprising that the expression of quite a variety of genes is altered in response to cellular injury in mammalian cells (4). These genes are of interest, in part, because of the possibility that changes in their expression can be used as a surrogate for the early detection of cellular injury and quantification of its extent.

Among the injury-inducible mammalian genes, GADD153 may be as a candidate for early detection of cellular injury because of the large magnitude of the increase in its mRNA. GADD153 was originally cloned by hybridization subtraction of mRNA from CHO cells before and after UV irradiation (5). It is one of 5 "growth arrest and DNA damage" genes found to be coordinately induced by either growth arrest or DNA damage (6). GADD153 is highly conserved in mammalian species; hamster GADD153 shares 78% nucleotide sequence identity with the human exons (7) and >85% with the mouse exons (8). Although the mechanism responsible for the activation of GADD153 expression after DNA damage is still unclear, current evidence suggests that the magnitude of the increase is proportional to the extent of cellular injury with maximal GADD153 promoter activity occurring under circumstances of severe toxicity to the cell (9–13).

Current in vitro detection of cellular injury is normally accomplished by measuring the number of cells that survive exposure to the drug. A variety of assays exist, but all of them require a period of several days to weeks of cell growth. The detection of cellular injury in vivo is much more problematic, and is generally measured as gross change in the size of a tumor mass in the living host. Current screening using tumor models for the evaluation of candidate compounds based on tumor growth delay or survival is costly, labor-intensive, relatively insensitive and requires days to weeks of monitoring.

In experimental systems there are several ways to monitor the GADD153 promoter activity as a surrogate for cellular injury detection. These include linking GADD153 promoter fragment to the coding sequences of the chloramphenicol acetyltransferase gene (10), the beta-galactosidase gene (14), and firefly (15) or bacterial luciferase gene (11, 16). The ability of those reporter enzymes to catalyze substrates reflects the activity of GADD153 promoter. However, such enzyme-related assays require additional substrates or cofactors, are inconvenient and of limited use with living tissue.

Hence, the prior art is deficient in the lack of an effective reporter system that can readily quantifies cellular injury and be adapted for high throughput in vitro and in vivo screening. The present invention fulfills this long-standing need and desire in the art.

SUMMARY OF THE INVENTION

The present invention consists of a molecularly engineered cell line that functions as a reporter system for the detection of cellular injury. To produce this cell line a chimeric gene containing the GADD153 promoter linked to the coding region of an enhanced green fluorescent protein (EGFP) gene was stably integrated into the genome of UMSCC10b head and neck carcinoma cells. The molecularly engineered cell line is identified as the T10b45 cell line. Activation of the GADD153 promoter within the T10b45 cells grown in vitro or in vivo by agents or environmental factors injurious to the cell that act via a wide variety of different mechanisms can be quantified using flow cytometric measurement of EGFP expression following the treatment. Moreover, the reporter system is able to discriminate the relative potency of drug-DNA adducts, making it feasible to utilize it to categorize analogs which produce similar types of DNA adducts.

The successful use of the GADD153 promoter to create the T10b45 reporter system validates the concept that injury-responsive promoters can be used to develop reporter systems. It would be obvious to someone skilled in the art that clones of either the UMSCC10b cells, or other types of cells, could be constructed using other injury-responsive promoters capable of reporting on the activation of specific intracellular pathways or specific types of cellular injury.

The present invention features a method to use GADD153-driven EGFP expression to monitor cellular injury induced by a variety of genotoxic agents such as DNA cross-linking and methylating agents, oxygen free radicals, DNA intercalators, UV and γ-radiation, and hypoxia.

The present invention also features a method to use GADD153-driven EGFP expression to monitor cellular injury in vivo.

In yet another embodiment of the present invention, there is provided a method to use GADD153-driven EGFP expression to categorize the relative potency of adducts produced by related platinum-containing drugs.

Other and further aspects, features, and advantages of the present invention will be apparent from the following description of the presently preferred embodiments of the invention given for the purpose of disclosure.

BRIEF DESCRIPTION OF THE DRAWINGS

So that the manner in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984). Therefore, if appearing herein, the following terms shall have the definitions set out below.

As used herein, the term "cDNA" shall refer to the DNA copy of the MRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J Biol. Chem., 243:3552–59 (1969), abbreviations for amino acid residues may be used.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. A "vector" may further be defined as a replicable nucleic acid construct, e.g., a plasmid or viral nucleic acid.

A "DNA molecule" refers to the polymeric form of deoxyribonucleotides (adenine, guanine, thymine, or cytosine) in its either single-stranded form or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. The structure is discussed herein according to the normal convention of giving only the sequence in the 5' to 3' direction along the nontranscribed strand of DNA (i.e., the strand having a sequence homologous to the mRNA).

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites and sequences which control the termination of transcription and translation. Methods which are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses. In general, expression vectors contain promoter sequences which facilitate the efficient transcription of the inserted DNA fragment and are used in connection with a specific host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are typically determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters typically contain Shine-Dalgarno ribosome-binding sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15–25 or more nucleotides, depending upon the complexity of the target sequence, although it may contain fewer nucleotides.

In the present invention, "cellular injury" refers to an act that damages or hurts the cell.

Fluorescence labeling is a particularly useful tool for marking a protein, cell, or organism of interest. Traditionally, a protein of interest is purified, then covalently conjugated to a fluorophore derivative. For in vivo studies, the protein-dye complex is then inserted into cells of interest using micropipetting or a method of reversible permeabilization. The dye attachment and insertion steps, however, make the process laborious and difficult to control. An alternative method of labeling proteins of interest is to concatenate or fuse the gene expressing the protein of interest to a gene expressing a marker, then express the fusion product. Typical markers for this method of protein labeling include β-galactosidase, firefly luciferase and bacterial luciferase. These markers, however, require exogenous substrates or cofactors and are therefore of limited use for in vivo studies.

A marker that does not require an exogenous cofactor or substrate is the green fluorescent protein (GFP) of the jellyfish Aequorea victoria, a protein with an excitation maximum at 395 nm, a second excitation peak at 475 nm and an emission maximum at 510 nm. Green fluorescent protein is a 238-amino acid protein, with amino acids 65–67 involved in the formation of the chromophore.

Uses of green fluorescent protein for the study of gene expression and protein localization are well known. The compact structure makes GFP very stable under diverse and/or harsh conditions such as protease treatment, making GFP an extremely useful reporter in general.

New versions of green fluorescent protein have been developed, such as a "humanized" GFP DNA, the protein product of which has increased synthesis in mammalian cells. One such humanized protein is "enhanced green fluorescent protein" (EGFP). Other mutations to green fluorescent protein have resulted in blue-, cyan- and yellow-green light emitting versions.

The GADD153 gene is strongly transcriptionally activated by many types of cellular injury, and the magnitude of the change in GADD153 expression is proportional to the extent of damage. In the present invention, a reporter system was developed in which a chimeric gene containing the GADD153 promoter linked to the coding region of an enhanced green fluorescent protein (EGFP) gene was stably integrated into the genome of UMSCC10b head and neck carcinoma cells, resulting in a cell line identified as T10b45. Activation of the GADD153 promoter was quantified using flow cytometric measurement of EGFP expression following drug exposure. The GADD153 promoter was activated by N-methl-N'-nitro-N-nitrosoguanidine (MNNG) in a concentration dependent manner with kinetics that closely paralleled perturbation of cell cycle phase distribution. EGFP expression was strongly activated by a variety of genotoxic agents including DNA cross-linking and methylating agents, oxygen free radicals, DNA intercalator, UV and γ-radiation, and hypoxia. When grown as a xenograft in nude mice, the stably transfected clone also demonstrated dose-dependent EGFP expression when measured 4 days after cisplatin treatment. The reporter system also accurately categorized the relative potency of adducts produced by 6 related platinum-containing drugs.

The ability of T10b45 cells to report quantitatively on the extent of cellular injury was demonstrated first using N-methl-N'-nitro-N-nitrosoguanidine. For this agent, there is a well-defined relationship between exposure concentration and cell kill, and a similar relationship was apparent for the degree of EGFP expression. When measurements were made at 4 days after drug exposure, the dynamic range of this reporter system extended from a lower limit of approximately 3.7 times the $IC_{50}$ (5 μM MNNG) to an upper limit of approximately 14.8 times the $IC_{50}$ (20 μM MNNG).

It is noteworthy that the EGFP level in T10b45 cells continued to increase for a full 6 days following an exposure to N-methl-N'-nitro-N-nitrosoguanidine at concentration that was equivalent to 14.8 times the $IC_{50}$. The half-life of EGFP in mammalian cells has been reported to be in the range of 24–48 hrs (18, 19). Thus, the results are consistent with conclusion that injury-related signals continued to stimulate the GADD153 promoter even during the late stages of the cellular injury response.

As another measure of the duration of the injury response, the extent of $G_2/M$ checkpoint arrest as a function of time was monitored. The perturbation of cell cycle phase distribution produced by a 4 hr exposure to 20 μM N-methl-N'-nitro-N-nitrosoguanidine was shown to persist through day 6 and to have resolved by day 8. Thus, there was good agreement regarding the kinetics of the cellular injury response as monitored by these two parameters. One implication of this finding is that the pathways signaling these two outcomes may be very similar or the same. Another implication is that this reporter system offers substantial flexibility with respect to when EGFP expression measurements can usefully be made; this is important with respect to potential in vivo applications.

Previous studies utilizing Northern blot analysis of GADD153 mRNA levels in UMSCC10b cells xenografted in nude mice treated with 50 mg/kg cisplatin showed that the GADD153 mRNA level was increased 3.0±0.4 (SD) -fold relative to that in tumors from untreated mice when measured at 24 hr post-treatment (12). The results obtained with the T10b45 cells suggest that measurement of the fraction of cells expressing EGFP is substantially more sensitive. At a dose of only 15 mg/kg, cisplatin produced a 29.2±6.2 (SD) -fold increase in the fraction of cells expressing EGFP.

Drugs that directly damage DNA produced the highest levels of EGFP expression among the panel of agents and types of injury tested. However, even among these agents there are clear differences in the magnitude of the effect indicating that the signal transduction pathways activated by even putatively closely related types of DNA damage are heterogeneous. For example, the data are consistent with the hypothesis that DNA adducts produced by the platinum drugs and by BCNU generate substantially different types of cellular injury responses. Because of this heterogeneity, it may be possible to use the T10b45 reporter system to categorize injurious agents based on whether or not the GADD153 promoter is activated, and thus identify common features among the responses produced by stresses as different as those imposed by hypoxia and platinum drug exposure.

The tumor microenvironment is characterized by regions of fluctuating hypoxia, low pH, and nutrient deprivation (20, 21). It was of particular interest that an episode of hypoxia, at levels commonly encountered in tumors, followed by return to a euoxic environment was as effective as some known DNA damaging agents, such as UV-irradiation, at activating EGFP expression. This finding is consistent with the concept that hypoxia followed by re-oxygenation can cause DNA damage. Welbourn et al (22) demonstrated that cells subjected to repeated cycles of hypoxia and reoxygenation have increased intracellular levels of superoxide and other bioactive oxygen radicals that can react with DNA directly. Hypoxia may also damage DNA indirectly by inducing endonuclease activity resulting in DNA strand breakage (23, 24). Russo et al (24) found that a 24 hr exposure to hypoxia increased the number of chromosomal breaks to ≈3-fold above the background, paralleling the expression of hypoxia-induced endonucleases. The ability of the T10b45 reporter system to detect hypoxic injury provides a tool with which to investigate the contribution of hypoxia as a determinant of genetic instability and malignant progression.

The fact that T10b45 cells can be used to detect cellular injury in vivo is another particularly important benefit of this reporter system. To be useful as a chemotherapeutic agent, a compound must produce significant tumor cell kill in vivo at doses that are tolerable to the host. Screening of candidate compounds using tumor growth delay or survival is costly, labor-intensive, and slow. It is encouraging that injury to T10b45 tumors growing subcutaneously was detectable even at a cisplatin dose of 5 mg/kg, which is well below the $LD_{10}$ for this drug. The fact that EGFP expression can be quantified in even very small tumors, and that multiple tumors of the same or different types can be implanted into the same animal, add additional degrees of freedom in the application of this reporter system to in vivo screening.

The results of the comparison of the 6 platinum-containing drugs used in this study was informative with respect of the analysis of adduct potency. Assessment of adduct potency is often of interest when screening large numbers of closely related analogs. In the case of the platinum-containing drugs, this has been done in the past by measuring the amount of Pt in the DNA at equal levels of cytotoxicity (25, 26). While it is clear that total DNA Pt is only a surrogate for the number of cytotoxically important adducts, this approach has nevertheless been useful in categorizing analogs. The T10b45 reporter system easily distinguished between adducts of differing potency, and yielded virtually the same information as the more cumbersome measurement of cytotoxic potency. The adducts produced by cisplatin and carboplatin, which have the same structure (27–29), were approximately equipotent with respect to triggering cell death and EGFP expression. The same was true of adducts produced by tetraplatin and oxaliplatin; the structure of these adducts is the same (30–32), but differs importantly from those produced by cisplatin and carboplatin, transplatin and JM216 (33, 34). Thus, there was a close association between the potency of a particular type of adduct with respect to causing cell death and activating the GADD153 promoter-mediated expression of EGFP.

The past decade has seen the development of combinatorial techniques that are capable of generating enormous libraries of structurally related compounds. These are of great interest as sources of novel chemotherapeutic agents. Because these compounds are likely to be useful as drugs only if they can actually enter cells and cause cell death, there is now an urgent need to develop high throughput systems capable of reporting on the actual degree of cellular injury produced in intact cells in vitro and in vivo. The novel reporter system in the present invention is suitable for high throughput in vitro and in vivo screening, and can be used for the development of a mechanism-based drug screening strategy to. detect agents capable of producing cytotoxicity via a wide variety of different mechanisms. It can also be used to classify injurious agents based on whether they activate the GADD153 promoter or not. Possible uses include, but are not limited to, the following:

(1) The screening of large libraries of chemicals to identify compounds that cause cellular injury for the purpose of discovering new drugs. For example, this cellular reporter system could be utilized for high throughput screening of synthetic combinatorial libraries, natural products derived from many sources, and agents designed on the basis of molecular modeling.

(2) The screening of agents to exclude those that cause cellular injury. For example, in developing new cosmetics, the reporter system could be used to exclude, at an early stage of development, compounds that cause cellular injury.

(3) The identification and quantification of interactions between injurious agents and other drugs, environmental factors, various types of irradiation, etc. For example, the reporter system could be used to identify agents that either increase or decrease the amount of injury produced by a known anticancer drug. It could also be used to screen for unwanted drug-drug interactions that could be injurious to the cell.

(4) The investigation of signal transduction pathways that turn on the GADD153 promoter. Quantification of GADD153 promoter activity by EGFP expression provides a tool with which to dissect how the different signal transduction pathways following a drug exposure communicate to turn on GADD153 promoter or distinguish the different mechanisms by which various agents cause cellular injury to cells.

(5) The screening of large numbers of structurally closely related analogs with respect to adduct potency. Because the T10b45 reporter system can readily distinguish between adducts of differing potency, it can be used to screen libraries of compounds with closely related structures to quantify their relative potency.

(6) Rapid in vivo quantification of tumor cell injury. Currently available systems for assaying antitumor activity in animals require laborious measurement of tumor volume over relatively long periods of times in large numbers of animals. T10b45 cells are particularly attractive as an alternative approach for the following reasons: a) they can be grown as xenografts; b) only small numbers of cells are required for measurement of the level of EGFP expression; c) multiple tumors can be inoculated in the same animal, permitting more powerful statistical analyses. Thus, the time and cost of the animal experimentation required for the development of a new cancer drug can be reduced, and the number of animals needed can be diminished.

The following examples are given for the purpose of illustrating various embodiments of the invention and are not meant to limit the present invention in any fashion.

EXAMPLE 1

Cell Lines

The UMSCC10b cell line was derived from a human head and neck squamous cell carcinoma (17). Cells were cultured at 37° C. under 5% $CO_2$ in RPMI 1640 (Mediatech Inc., Herndon, Va.) containing 10% fetal bovine serum (Gemini Bioproducts Inc., Calabasas, Calif.), 2 mM L-glutamine, and 100 units/ml penicillin G and 100 µg/ml streptomycin sulfate.

EXAMPLE 2

Vector Construction and Transfection

The pGADD153-EGFP (FIG. 1) was constructed in several steps. Plasmid pBS-GADD153 was created by ligating the ClaI/HindIII fragment of p9000 (from Dr. N. J. Holbrook, National Institute on Aging, Baltimore, Md.), containing the hamster GADD153 promoter, into the AccI/HindIII site of pBluescriptII KS(+/−). The EGFP cDNA was removed from pEGFP-N1 (CLONTECH Laboratories, Palo Alto, Calif.) with restriction enzymes BamHI and NotI, and was inserted into the BamHI/NotI site of pBS-GADD153 downstream of GADD153 promoter. The cassette consisting of the SV40 early promoter, puromycin resistance gene and SV40 poly $A^+$ sequences was removed from the pPUR selection vector (Clontech Laboratories, Palo Alto, Calif.) by digesting with PvuII and BamHI, and cloned into the KpnI site of pGADD153-EGFP by blunt end ligation. pGADD153-EGFP was introduced into UMSCC10b cells by transfection using lipofectin (Life Technologies) according to the manufacturer's instructions. Transfected cells were selected for 14 days in the presence of 3 µg/ml puromycin (Gibco). The puromycin-resistant clones were individually expanded into cell lines and screened by flow cytometry for the extent of EGFP expression 4 days following a 4 hr exposure to 20 µM N-methl-N'-nitro-N-nitrosoguanidine. One clone (T10b45) of 47 assayed was found to have MNNG-inducible EGFP expression, and this clone was used for all subsequent experiments. T10b45 cells were maintained in medium supplemented with 3 µg/ml puromycin.

EXAMPLE 3

Quantitation of GFP Expression Level by Flow Cytometry

T10b45 cells were harvested 4 days following exposure to the injurious agent, washed once and resuspended in PBS. Cytometric analysis was performed using a Becton Dickinson (Mountain View, Calif.) FACScan equipped with an argon ion laser tuned to 488 nm to excite EGFP, and a 515/545 bandpass filter to monitor the green fluorescence emitted by EGFP. The acquired data were analyzed with the CELLQuest program. Twenty thousand events were collected for each sample. An analytical gate was set such that less than 0.2% of the untreated cells exceeded the gate. The relative fold induction was calculated by dividing the percent of treated cells in the gated region by that of untreated cells harvested at same time.

EXAMPLE 4

Determination of Cell Cycle Phase Distribution

Cells growing at subconfluent density in 6 cm tissue culture dishes were exposed to 25 µM N-methl-N'-nitro-N-nitrosoguanidine for 4 hours. At 1, 2, 3, 4, 5, 6, 7, 8 days after N-methl-N'-nitro-N-nitrosoguanidine treatment, cells were harvested by trypsinization, washed twice with ice-cold PBS, fixed in ice-cold 70% ethanol, treated with RNase(Sigma) at 37° C. for 30 min, and stained with 50 µg/ml propidium iodide (Sigma). After a 30 min incubation on ice, the cells were analyzed on a FACScan flow cytometer (Becton-Dickinson, San Jose, Calif.) using the FlowJo cell cycle analysis software (Tree Star, Inc., San Carlos, Calif.) and the "Watson Pragmatic" model.

EXAMPLE 5
Chemical Agents and Treatment

Three hundred thousand T10b45 cells were seeded into 60 mm tissue culture dishes and treated 24 h later so that all experiments were performed with cells in the logarithmic phase of growth. The chemical agents were added directly to the tissue culture media. At the indicated times, the medium was removed and the cells were washed twice with serum-free medium and then incubated for 4 days in fresh drug-free medium at 37° C. following which they were subjected to flow cytometric analysis.

5-Fluorouracil, etoposide, paclitaxel, hydrogen peroxide, actinomycin D, aphidicolin, N-methl-N'-nitro-N-nitrosoguanidine, transplatin, tetraplatin and doxorubicin were purchased from Sigma Chemical Co. (St. Louis, Mo.). Cisplatin, carboplatin, JM216 and BCNU were obtained from Bristol-Myers Squibb Co. (Princeton, N.J.). Oxaliplatin was a gift from Sanofi Pharmaceuticals (Malvern, Pa.). Raltitrexed was a gift from Zeneca Pharmaceuticals (Macclesfield, Cheshire U.K.). Topotecan was purchased from SmithKline Beecham Pharmaceuticals (King of Prussia, Pa.). Doxorubicin and the clinical formulation of gemcitabine were obtained from Eli Lilly and Co. (Indianapolis, Ind.) and Ben Venue Laboratories (Syracuse, N.Y.), respectively.

Hypoxia was achieved by culturing T10b45 cells at 37° C. in complete medium in a 7 liter air-tight chamber. The chamber was flushed with 95% $N_2$/5% $CO_2$ for 15 min at a flow rate of 20 liters/min. Anaerobic conditions were confirmed using BBL Dry Anaerobic Indicator Strips (Becton Dickinson, Cockeysville, Md.), which determined the oxygen content in the chamber to be between 0 and 0.1%. Cells were kept under hypoxic conditions for 48 hrs and subjected to flow cytometric analysis after a subsequent 4 day incubation in a normoxic environment.

Irradiation with 30 $J/m^2$ UV was carried out using a germicidal lamp at a dose rate of 0.045 $J/m^2/s$ at 254 nm, and γ-radiation was performed by exposing cells to a $^{137}$Cs source (GammaCell 40) to deliver a dose of 20 Gy.

Growth arrest by media depletion was accomplished by incubating exponentially growing cells at a density of $1\times10^7$ cells/6 cm dish for 96 hr without replenishing the culture medium. During this period of time, the culture became confluent and the medium was depleted of growth factors and many nutrients.

EXAMPLE 6
In Vivo Experiments

T10b45 cells in log phase were harvested by trypsinization, washed in PBS, and resuspended with serum-free culture medium at a concentration of $1\times10^7$ cells/ml before s.c. injection into mice. Female athymic (BALB/c nu/nu) mice, 7~8 weeks old (Harlan Sprague Dawley, Indianapolis, Ind.), were implanted with $1\times10^6$ cells at each of 4 sites (left and right axillary and flank regions). When the average tumor size reached 100 $mm^3$, the mice were randomized into a control group (drug vehicle) and 3 cisplatin treatment groups designated to receive single doses of 5, 10, and 15 mg/kg by the i.p. route. All animals were euthanized 4 days later, and the tumors were harvested and disaggregated using a cocktail of 0.1% collagenase type I and 0.01% Dnase in $Ca^{++}/Mg^{++}$- free medium containing 0.02% EDTA to produce a single cell suspension. The cells were immediately subjected to flow cytometric analysis to quantify the fraction of EGFP-expressing cells.

EXAMPLE 7
Clonogenic Assay

The sensitivity of T10b45 cells to various platinum-containing drugs and N-methl-N'-nitro-N-nitrosoguanidine was determined by clonogenic assay. Cisplatin, carboplatin, oxaliplatin were dissolved immediately before use in 0.9% NaCl at 1 mM, whereas stock solutions of transplatin, tetraplatin, JM216 and N-methl-N'-nitro-N-nitrosoguanidine was prepared in DMSO. The final concentration of DMSO in the culture was <0.1% at all drug concentrations and in controls. Clonogenic assays were performed by seeding 300 cells into 60 mm plastic dishes in 5 ml of complete media. After a 24 hour incubation at 37° C., appropriate amounts of the drugs were added to the dishes and incubated for 1 hour for all the platinum-containing drugs or for 4 hours for N-methl-N'-nitro-N-nitrosoguanidine, after which the cells were washed and fresh medium was replaced. Colonies of at least 50 cells were scored visually after 14 days. Each experiment was performed a minimum of 3 times using triplicate cultures for each drug concentration. $IC_{50}$ values were determined using log-linear interpolation.

EXAMPLE 8
Platinum-DNA Adduct Formation

To measure platinum-DNA adduct formation, T10b45 cells were exposed for 1 hour to cisplatin, carboplatin, oxaliplatin, transplatin, tetraplatin and JM216 at concentrations $10\times IC_{50}$, washed three times with PBS, and incubated overnight at room temperature in a lysis buffer containing 0.67% Triton X-100, NaCl 2.6 M, 133 mM EDTA, and 2.6 M Tris-HCl (pH 8.0). DNA was isolated by phenol-chloroform extraction and dissolved in TE buffer (pH 8.0). Aliquots of the DNA were digested in 1 M HCl at 75° C. for 2 hours and the hydrolysate was used for the quantitation of Pt by flameless atomic absorption spectrophotometry (Perkin-Elmer Model 2380).

Figure 1:
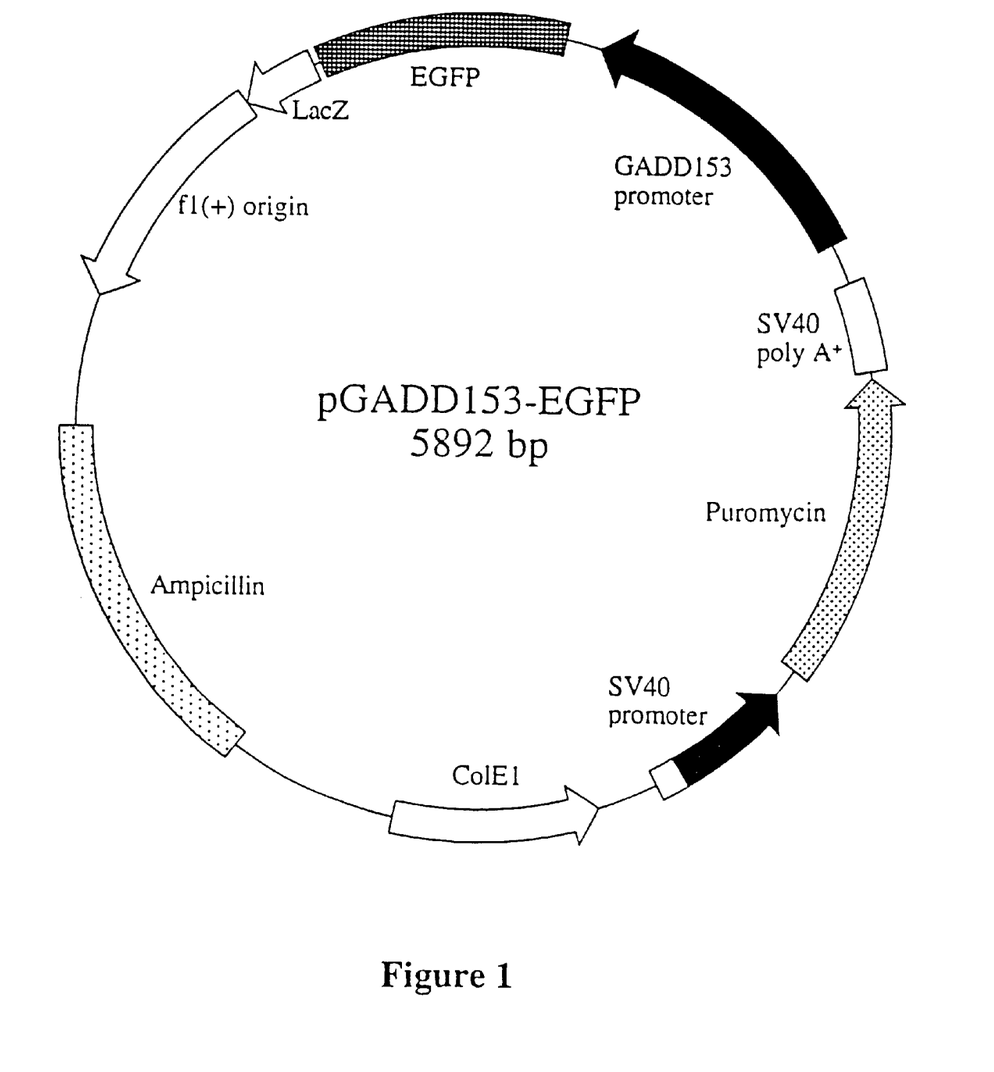
FIG. 1 shows the schematic map of the expression vector pGADD153-EGFP.
Figure 2:
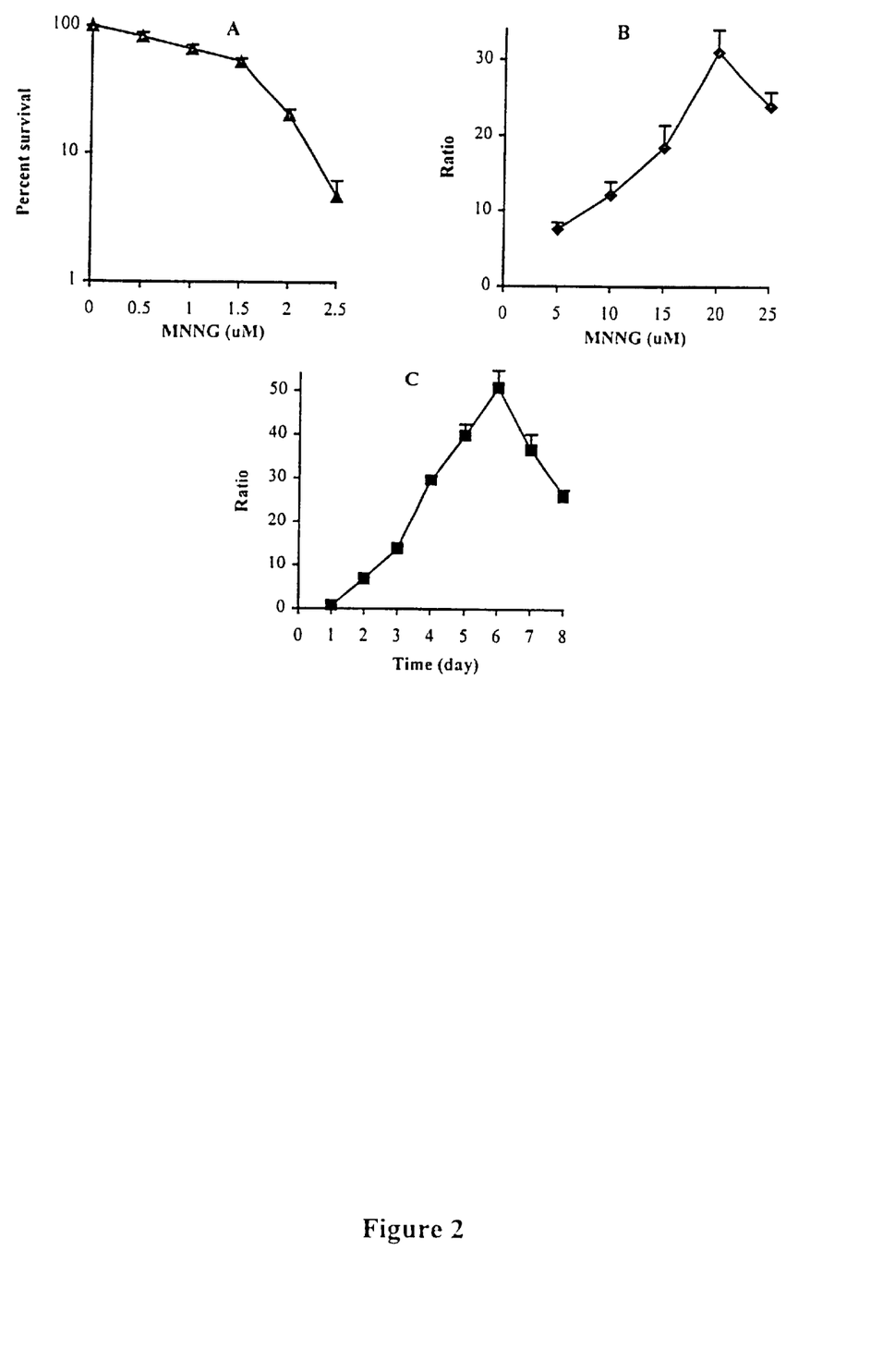
FIG. 2 shows the effect of exposure to N-methl-N'-nitro-N-nitrosoguanidine (MNNG) on cell kill and induction of EGFP expression. Panel A: Clonogenic survival curve for T10b45 cells exposed to increasing concentrations of N-methl-N'-nitro-N-nitrosoguanidine for 4 hours. Panel B: Fold increase in the fraction of cells expressing EGFP as a function of N-methl-N'-nitro-N-nitrosoguanidine concentration measured by flow cytometric analysis 4 days after a 4 hr drug exposure. Panel C: Fold increase in the fraction of cells expressing EGFP as a function of time following a 4 hr exposure to 20 $\mu$M N-methl-N'-nitro-N-nitrosoguanidine. Each data point represents the mean of three experiments performed with triplicate cultures. Error bars, ±_SD.

EXAMPLE 9
Concentration-Response and Kinetics of Induction After N-methl-N'-nitro-N-nitrosoguanidine (MNNG) Treatment FIG. 1 shows a map of the pGADD153-EGFP vector in which the GADD153 promoter is positioned to drive transcription of EGFP. pGADD153-EGFP was transfected into UMSCC10b cells to produce the T10b45 clone capable of expressing EGFP in response to cellular injury. FIG. 2A shows the concentration-survival curve, measured by clonogenic assay, produced by 4 hour exposure to N-methl-N'-nitro-N-nitrosoguanidine. The $IC_{50}$ was 1.36±0.05 uM. To determine concentration-response curve for the activation of GADD153-EGFP expression by N-methl-N'-nitro-N-nitrosoguanidine in T10b45 cells, cultures were treated with 5, 10, 15, 20, 25 μM N-methl-N'-nitro-N-nitrosoguanidine for 4 hrs and flow cytometric analysis for EGFP expression was performed 4 days later. FIG. 2B shows that GADD153-EGFP induction increased in proportion to N-methl-N'-nitro-N-nitrosoguanidine concentration up to 20 μM; at an even higher concentration of 25 μM, EGFP expression began to decrease.

Figure 3:
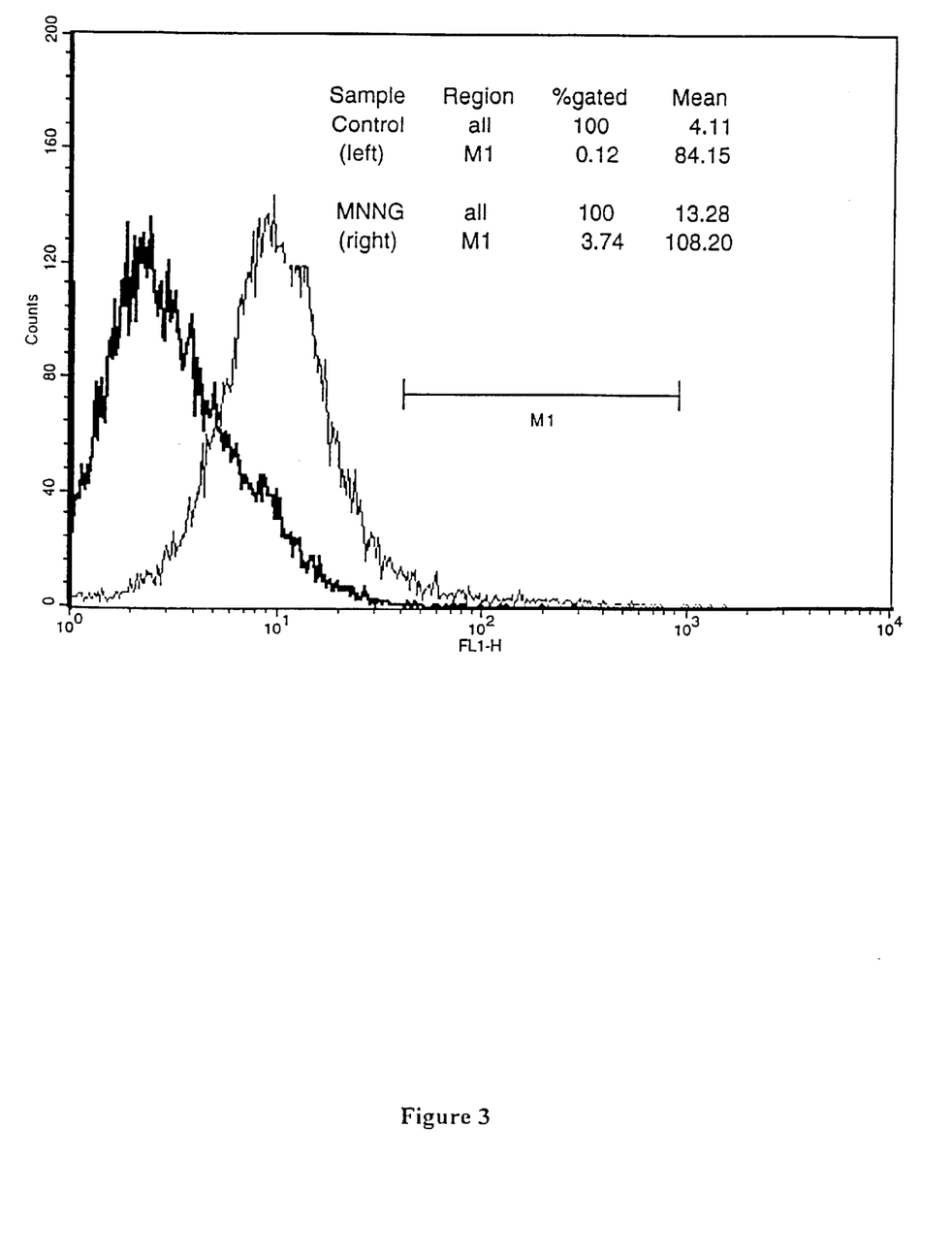
FIG. 3 shows the detection of GFPin T10b45 cells by flow cytometry. Left curve, control cells; Right curve, cells exposed to 20 $\mu$M N-methl-N'-nitro-N-nitrosoguanidine for 4 hours and harvested at day 4. The gated region M1 was fixed as described below.

The actual distribution of cellular fluorescence intensity is shown in FIG. 3. Four days after challenging with 20 μM N-methl-N'-nitro-N-nitrosoguanidine for 4 hour, the fluorescence of T10b45 cells increased from a mean channel value of 4.11 (comparable to untreated control cells) to 13.28, and cells falling within the gated region increased from 0.12% to 3.74%.

The time course of GADD153-EGFP expression following a 4 hour exposure to 20 μM N-methl-N'-nitro-N- nitrosoguanidine is shown in FIG. 2C. GADD153-EGFP expression was detectable by day 2, and increased approximately linearly with time until it peaked at day 6. These results established that EGFP expression in T10b45 cells quantitatively reported on the extent of cellular injury due to N-methl-N'-nitro-N-nitrosoguanidine.

EXAMPLE 10

Duration of $G_2$-M Arrest Induced by MNNG

Figure 4:
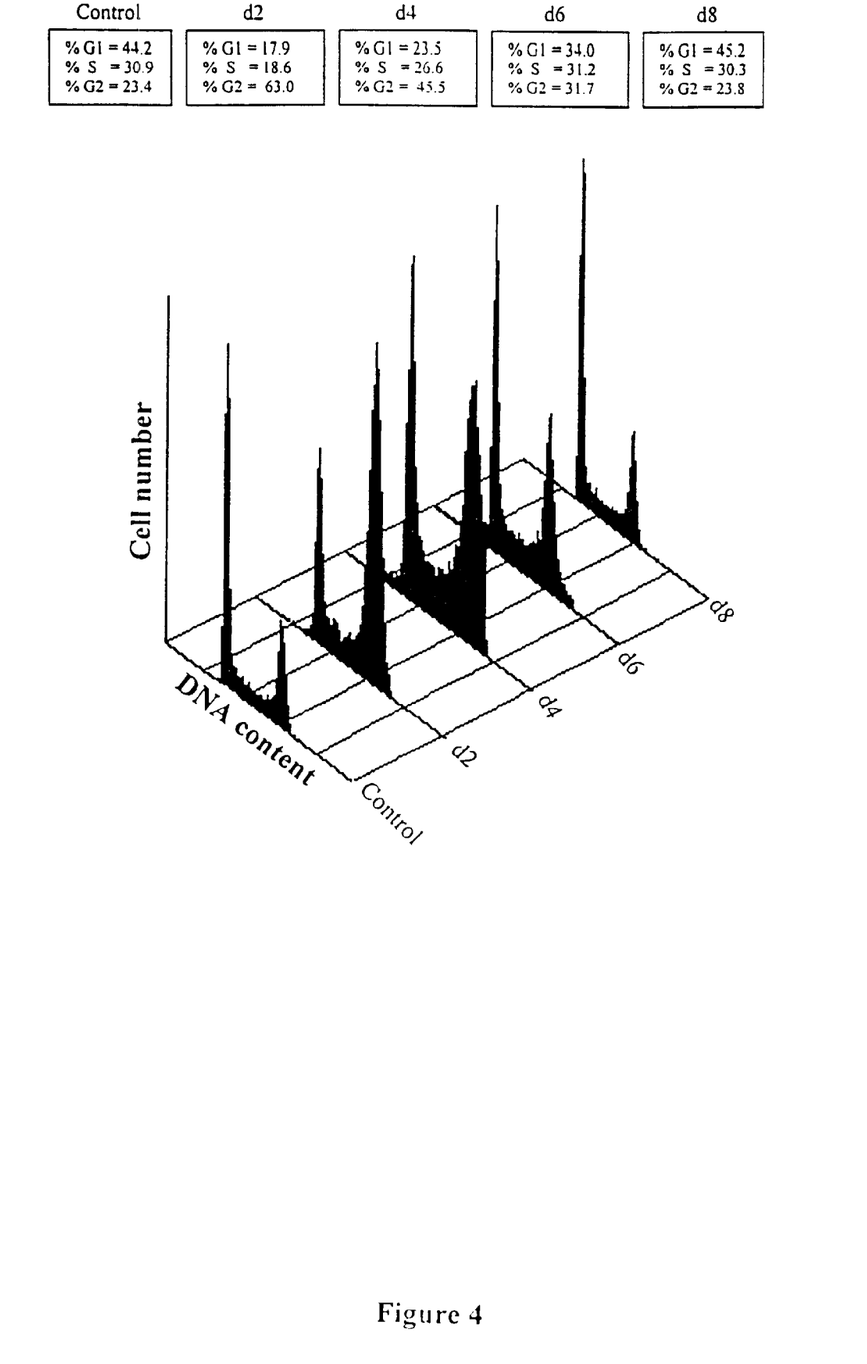
FIG. 4 shows the change in cell cycle phase distribution at times up to 8 days following a 4 hour exposure to 20 $\mu$M N-methl-N'-nitro-N-nitrosoguanidine measured by flow cytometry.

Cell cycle analysis was performed to determine the duration of the cellular injury response after a 4 hour exposure to 20 μM N-methl-N'-nitro-N-nitrosoguanidine. As shown in FIG. 4, $G_2$/M phase arrest was maximal at 2 days when the 63.0% of the treated cells were in $G_2$ or M phase compared to 23.4% of the cells in the untreated control population. The N-methl-N'-nitro-N-nitrosoguanidine-induced perturbation of cell cycle phase distribution persisted for 6 days, and had resolved completely by 8 days after the drug exposure. Thus, the duration of the injury response detected by activation of the GADD153 promoter closely matched the duration of the cell cycle phase perturbation.

EXAMPLE 11

Types of Cellular Injury That Induce EGFP Expression

T10b45 cells were screened for EGFP expression following many different kinds of cellular injury, and the results are summarized in Table 1. For each type of injury, EGFP expression 4 days after the insult was measured as a function of the intensity or duration of injury.

Table 1 presents the data for the concentrations or schedules that yielded maximal activation of the GADD153 promoter based on concentration-response and kinetic studies. The types of injury that strongly activated the EGFP expression included those due to the DNA cross-linking agents tetraplatin, oxaliplatin, cisplatin, carboplatin, and JM216, the DNA methylating agent N-methl-N'-nitro-N-nitrosoguanidine, oxygen free radicals produced by hydrogen peroxide, UV and γ-radiation, the DNA intercalator actinomycin D, and hypoxia. The magnitude of the peak induction ranged from 6- to 143-fold relative to untreated T10b45 cells. Among the direct DNA-damaging agents tested, only transplatin and BCNU failed to produce significant activation.

Interestingly, cellular injury due to exposure to 3 different antimetabolites 5-fluorouracil, gemcitabine and raltitrexed, the anthracyclene doxorubicin, representative topoisomerase I and II inhibitors topotecan and etoposide, the microtubulin damage agent paclitaxel, DNA and RNA synthesis inhibitor aphidicolin and doxorubicin, and medium depletion was relatively impotent with respect to induction of EGFP expression. Thus, substantial differences were detected in the responsiveness of T10b45 cells to different types of cellular injury. This heterogeneity of response offers the opportunity to categorize injurious agents on the basis of their ability to activate the signal transduction pathways that regulate GADD153 promoter activity rather than just on the basis of their putative intracellular targets.

TABLE 1

Induction of GADD153 promoter activity in T10b45 cells following various cell treatments

| Agent/Type of Injury | Concentration | Time (h) | Induction Ratio* |
|---|---|---|---|
| Antimetabolites | | | |
| 5-Fluorouracil | 50 μM | 4 | 3.0 |
| Gemcitabine | 50 nM | 4 | 0.6 |
| Raltitrexed | 50 nM | 4 | 0.6 |
| DNA and RNA synthesis inhibitors | | | |
| Aphidicolin | 20 μM | 24 | 2.5 |
| Doxorubicin | 100 nM | 4 | 2.4 |
| DNA intercalator | | | |
| Actinomycin D | 50 μM | 4 | 7.6 |
| Topoisomerase inhibitors | | | |
| Topotecan | 20 nM | 4 | 1.3 |
| Etoposide | 5 μM | 4 | 4 |
| Microtubulin damaing agent | | | |
| Paclitaxel | 70 nM | 4 | 2.8 |
| Alkylating agent | | | |
| BCNU | 100 μM | 4 | 4 |
| DNA methylating agent | | | |
| MNNG | 20 μM | 4 | 31 |
| Bulky DNA adducts | | | |
| UV radiation | 30 J/m$^2$ | | 6 |
| γ-radiation | 20 Gy | | 9 |
| Free radical producers | | | |
| Hydrogen peroxide | 500 μM | 1 | 13 |
| DNA cross-linking agents | | | |
| Cisplatin | 50 μM | 1 | 42 |
| Carboplatin | 200 μM | 42 | 33 |
| Oxaliplatin | 50 μM | 1 | 105 |
| Transplatin | 500 μM | 1 | 1 |
| Tetraplatin | 50 μM | 1 | 143 |
| JM216 | 150 μM | 1 | 43 |
| Hypoxia | $O_2 < 0.1\%$ | 48 | 6 |
| Medium depletion | | 96 | 1.2 |

*Exponentially growing T10b45 cells were treated with the indicated agents and times, and GFP induction was determined 4 days after treatment by flow cytometry. The induction ratio refers to the percent of GFP expressing cells observed following the treatment relative to the untreated control GFP expressing fraction.

EXAMPLE 12

Activation of EGFP Expression In Vivo

Demonstration of a quantitative relationship between cellular injury and EGFP expression in vitro suggested that it might be possible to use T10b45 cells to quantify cellular injury following drug treatment in vivo as well. To test this concept, T10b45 cells were xenografted s.c. into BALB/c nu/nu mice. The resulting tumors were allowed to grow to an average volume of 100 mm$^3$, and then the mice were treated with 0, 5, 10, or 15 mg/kg cisplatin administered as a single intraperitoneal injection. The tumors were harvested 4 days after drug treatment and subjected to flow cytometric analysis.

Figure 5:
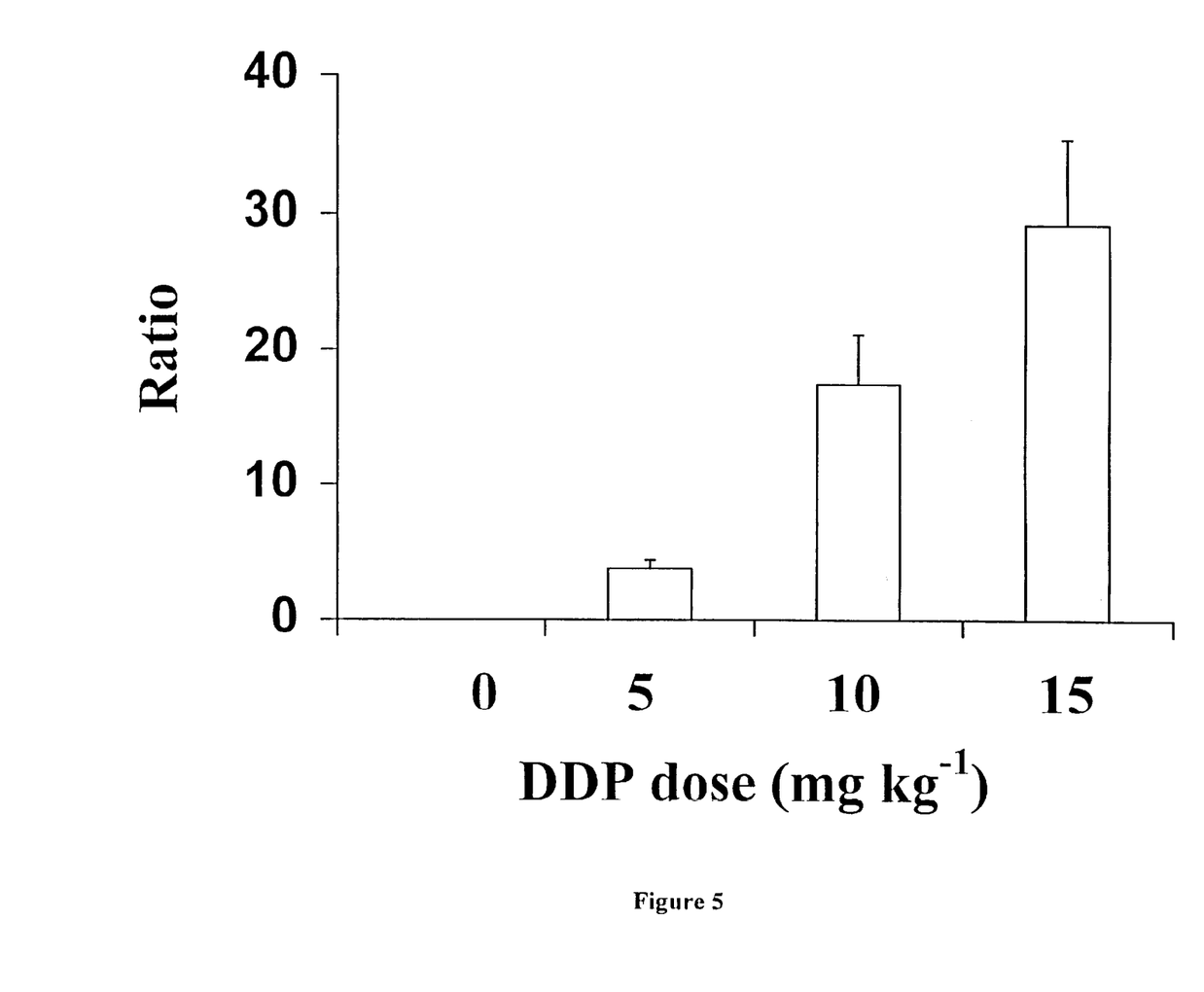
FIG. 5 shows the ratio of the percent of EGFP-expressing cells in cisplatin-treated versus untreated tumors as a function of dose. Mice bearing T10b45 xenografts were treated with cisplatin 0, 5, 10, 15 mg/kg, and the cells were harvested and analyzed by flow cytometry 4 days later. Values are reported relative to tumors from untreated animals. Error bars, ±SD.

Cisplatin increased the fraction of cells in T10b45 xenografts that expressed EGFP in a dose-dependent manner similar to that observed following in vitro exposure. In the untreated control tumors, 0.13±0.02 (SD) % of the cells expressed EGFP whereas following a cisplatin dose of 15 mg/kg 3.8±0.8 (SD) % of the tumor cells expressed EGFP. FIG. 5 presents the data in terms of the ratio of the fraction of cells expressing EGFP in the treated relative to the untreated tumors as a function of dose. For reference, the $LD_{10}$ for cisplatin in this strain is 12 mg/kg. At a dose of 15 mg/kg, cisplatin increased the fraction of EGFP expressing cells by a factor of 29-fold. However, even at the relatively low dose of 5 mg/kg cisplatin produced a readily quantifiable 3.8- fold increase in the fraction of EGFP-expressing cells to 0.49±0.5 (SD) %.

EXAMPLE 13

Relative Potency of Structurally Related Platinum DNA Adducts

One potential use for a cellular injury reporter system such as the T10b45 cells is to screen libraries of compounds with closely related structures to identify cytotoxins and quantify their relative potency. Thus, it was of interest to determine whether the T10b45 cells could detect subtle differences in the potency of adducts produced by different members of a single class of chemotherapeutic agents. Given the high potency of the platinum-containing drugs, and the availability of analogs that produce adducts with different types of structures, the T10b45 cells were used to examine the relationship between cytotoxicity as measured by clonogenic assay, the extent of platinum-DNA adduct formation as measured by Pt/μg DNA at the end of a 1 hr drug exposure, and induction of EGFP expression at 4 days. The relative potency of each type of adduct with respect to cytotoxicity was expressed in terms of the amount of Pt in the DNA following exposure to equitoxic concentrations of drug. The relative potency of each type of adduct with respect to activation of the GADD153 promoter was expressed as the quotient of the fold increase in the fraction of the cells expressing EGFP and the amount of Pt in the DNA when cells were exposed to equitoxic concentrations.

As shown in Table 2, the relative potencies of platinum-DNA adducts varied markedly among the six platinum complexes tested. In terms of cytotoxicity, the rank order of adduct potency was: tetraplatin >oxaliplatin>carboplatin>cisplatin>JM216 >transplatin. Within the limits of experimental error, the rank order of potency for activation of EGFP expression was essentially the same. Thus, per μg Pt introduced into the DNA, tetraplatin was the most cytotoxic analog and also the most effective at activating EGFP expression. At the other end of the spectrum, per μg Pt introduced into the DNA, transplatin was the least cytotoxic and the least effective at activating EGFP expression. Thus, the potency of each type of adduct with respect to activation of EGFP expression faithfully mirrored the cytotoxic potency of the adduct, and differences in adduct potency were as readily quantified using EGFP expression as they were using a measure of cytotoxicity.

TABLE 2

Relative potency of platinum-DNA adducts with respect to cytotoxicity and activation of EGFP expression

| Drug | $IC_{50}$ (μM)* | GFP fold induction at 10 × $IC_{50}$ | Pg Pt/μg DNA a 10 × $IC_{50}$ | Relative EGFP activation potency (fold induction/ng Pt/ug DNA) at 10 × $IC_{50}$ |
|---|---|---|---|---|
| Cisplatin | 4.2 ± 0.03 | 38 ± 3.2 | 46.5 ± 3.3 | 825.0 ± 29.4 |
| Carboplatin | 10.7 ± 0.83 | 23 ± 2.6 | 30.7 ± 3.6 | 750.4 ± 22.1 |
| Tetraplatin | 3.3 ± 0.17 | 120 ± 7.8 | 11.5 ± 0.8 | 10482.7 ± 516.9 |
| Oxaliplatin | 5.1 ± 0.29 | 100 ± 5.3 | 18.4 ± 2.9 | 5496.0 ± 655.6 |
| JM216 | 4.5 ± 0.35 | 11 ± 3.2 | 161.1 ± 14.3 | 70.6 ± 20.5 |
| Transplatin | 379.2 ± 31.57 | 10 ± 2.0 | 242.2 ± 3.0 | 41.3 ± 8.5 |

*$IC_{50}$ was determined by colony-forming assay. Fold induction and Pt-DNA adducts were measured by flow cytometry and atomic absorption spectrophotometry, respectively, at concentrations 10 times the $IC_{50}$. Values reported are mean ± SD, n = 3.

As described in detail supra, the present invention provides a cell line useful in monitoring cellular injury, said cell line containing an expression vector comprising the coding sequence of an fluorescent protein gene linked to an injury-responsive promoter, wherein the promoter activity of said promoter is activated by cellular injury. In one aspect, the cell is a cancer cell. In a preferred embodiment, the cell line is T10b45. Although any injury-responsive promoter may be used in the methods of the present invention, the GADD153 promoter is preferred. The cell line of present invention may be used to monitor cellular injury caused by agents such as DNA cross-linking agents, DNA methylating agents, oxygen free radicals, DNA intercalator, UV radiation, gamma radiation, hypoxia, and platinum-containing chemotherapeutic drugs. In the methods of the present invention, any fluorescent protein is potentially useful but a preferred protein is enhanced green fluorescent protein.

The present invention is also directed to a method of screening candidate compounds that cause cellular injury, comprising the steps of: contacting a cell line with a candidate compound or a control compound that does not cause cellular injury to a cell, said cell line contains an expression vector comprised of the coding sequence of an fluorescent protein gene linked to an injury-responsive promoter, wherein the expression of fluorescent protein is induced in response to cellular injury; and measuring the expression of fluorescent protein, wherein an increased fluorescent protein expression by said candidate compound compared to control compound indicates said candidate compound causes cellular injury. In a preferred embodiment, the cell line is T10b45. Although any injury-responsive promoter may be used in the methods of the present invention, the GADD153 promoter is preferred. In the methods of the present invention, any fluorescent protein is potentially useful but a preferred protein is enhanced green fluorescent protein. A representative method of measuring the expression of fluorescent protein is by flow cytometry.

The present invention is also directed to a method of screening candidate compounds that cause cellular injury in an animal, comprising the steps of: implanting a cell line into said animal, said cell line contains an expression vector comprises of the coding sequence of an fluorescent protein gene linked to an injury-responsive promoter, wherein the expression of fluorescent protein is induced in response to cellular injury; treating said animal with a candidate compound or a control compound that does not cause cellular injury; and measuring the expression of fluorescent protein, wherein an increased fluorescent protein expression by said candidate compound compared to control compound indicates said candidate compound causes cellular injury. In a preferred embodiment, the cell line is T10b45. Although any injury-responsive promoter may be used in the methods of the present. invention, the GADD153 promoter is preferred. In the methods of the present invention, any fluorescent protein is potentially useful but a preferred protein is enhanced green fluorescent protein. A representative method of measuring the expression of fluorescent protein is by flow cytometry.

The present invention is also directed to a method of screening a library of candidate compounds with closely related structure and quantifying their relative potency in causing cellular injury, comprising the steps of: contacting a cell line with a library of candidate compounds or a control compound that does not cause cellular injury, said cell line contains an expression vector comprises of the coding sequence of an fluorescent protein gene linked to an injury-responsive promoter, wherein the expression of fluorescent protein is induced in response to cellular injury; and measuring the expression of fluorescent protein, wherein the level of green fluorescent protein expression induced by a candidate compound correlates with said candidate compound's potency in causing cellular injury, wherein the increase of fluorescent protein expression induced by a candidate compound compared to control compound correlates with said candidate compound's potency in causing cellular injury. In a preferred embodiment, the cell line is T10b45. Although any injury-responsive promoter may be used in the methods of the present invention, the GADD153 promoter is preferred. In the methods of the present invention, any fluorescent protein is potentially useful but a preferred protein is enhanced green fluorescent protein. A representative method of measuring the expression of fluorescent protein is by flow cytometry.

The following references were cited herein:
1. Walker G C. Induction DNA repair systems. Ann. Review Biochem., 54:425–57, 1985.
2. Weinhert T A and Hartwell L H. The RAD9 gene controls the cell cycle response to DNA damage in *Saccaromyces cervisiae*. Science, 241:317–22, 1988.
3. Rowley R, Hudson J and Young P G. The weel protein kinase is required for radiation-induced mitotic delay. Nature, 356:353–5, 1992.
4. Holbrook N J and Fornace A J Jr. Response to adversity: molecular control of gene activation following genotoxic stress. New Bbiologist, 3:825–33, 1991.
5. Fornace A J Jr, Alamo I and Hollander M C. DNA damage-inducible transcripts in mammalian cells. Proc. Natl. Acad. Sci. USA, 85:8800–4, 1988.
6. Fornace A J Jr, Nebert D W, Hollander C, Luethy J D, Papathanasiou M, Fargnoli J, et al. Mammalian genes coordinately regulated by growth arrest signal and DNA damaging agents. Mol. Cell. Biol., 9:4196–4203, 1989.
7. Park J S, Luethy J D, Wang M G, Fargnoli J, Fornace A J Jr, Mcbride OW, et al. Isolation, characterization and chromosomal localization of the human GADD153 gene. Gene, 116:259–67, 1992.
8. Ron D, and Habener J F. CHOP, a novel developmentally regulated nuclear protein that dimerizes with transcription factors C/EBP and LAP and functions as a dominant negative inhibitor of gene transcription. Genes Devel., 6:439–53, 1992.
9. Luethy J D, Fargnoli J, Park J S, Fornace A J Jr, Holbrook N J. Isolation and characterization of the hamster gadd153 gene. J. Biol. Chem., 265:16521–6, 1990.
10. Luethy J D, and Holbrook N J. Activation of the gadd153 promoter by genotoxic agents: a rapid and specific response to DNA damage. Cancer Res., 52:5–10, 1992.
11. Gately D P, Sharma A, Christen R, and Howell S B. Cisplatin and taxol activate different signal pathways regulating cellular injury-induced expression of GADD153. Brit. J. Cancer, 73:18–23, 1996.
12. Gately D P, Sharma A, Christen R, Barton R, Los G., and Howell S B. Induction of growth arrest and DNA damage inducible gene gadd153 by cisplatin in vitro and in vivo. Brit. J. Cancer, 70:1102–6, 1994.
13. Friedman A D. GADD153/CHOP, a DNA damage-inducible protein, reduced CAAT/enhancer binding protein activities and increased apoptosis in 32D cl3 myeloid cells. Cancer Res., 56:3250–6, 1996.
14. Silhavy T J, and Beckwith J R. Uses of lac fusions for the study of biological problems. Microbiol. Rev., 49:398–418, 1985.
15. Gould S J, and Subramani S. Firefly luciferase as a tool in molecular and cell biology. Anal. Biochem., 175:5–13, 1988.
16. Gately D P, and Howell S B. Paclitaxel activation of the GADD153 promoter through a cellular injury response element containing an essential Sp1 binding site. J. Biol. Chem., 271:20588–20593, 1996.
17. Grenman R, Burk D, Virolainen E, Buick R N, Church J, Schwartz D R, et al. Clonogenic cell assay for anchorage-dependent squamous carcinoma cell lines limiting dilution. Intl. J. Cancer, 44:131–6, 1989.
18. Yang T T, Cheng L, Kain S R. Optimized codon usage and chromophore mutations provide enhanced sensitivity with the green fluorescent protein. Nucleic Acids Res., 24:4592–3, 1996.
19. Cormack B P, Valdivia R H and Falkow S. FACS-optimized mutants of the green fluorescent protein (GFP). Gene, 173:33–8, 1996.
20. Moulder J E and Rockwell S. Tumor hypoxia: its impact on cancer therapy. Cancer Metastasis Rev., 5:313–341, 1987.
21. Rockwell S. Use of hypoxia-directed drugs in the therapy of solid tumors. Semin. Oncol., 19:29–40, 1992.
22. Welbourn C R, Goldman G, Paterson I S, Valeri C R, Shepro D, Hechtman H B. Pathophysiology of ischaemia reperfusion injury: central role of the neutrophil. Brit. J. Surg., 78:651–5, 1991.
23. Stoler D L, Anderson G R, Russo C A., Spina A M, Beerman T A. Anoxia-inducible endonuclease activity as a potential basis of the genomic instability of cancer cells. Cancer Res., 52:4372–8, 1992.
24. Russo C A., Weber T K, Volpe C M, Stoler D L, Petrelli N J, Rodriguez-Bigas M, et al. An anoxia inducible endonuclease and enhanced DNA breakage as contributors to genomic instability in cancer. Cancer Res., 55:1122–8, 1995.
25. Johnson S W, Shen D W, Pastan I, Gottesman M M, and Hamilton T C. Cross-resistance, cisplatin accumulation, and platium-DNA adduct formation and removal in cisplatin-sensitive an resistant human hepatoma cell lines. Exp. Cell Res., 226:133–9, 1996.
26. Johnson S W, Laub P B, Beesley J S, Ozols R F, and Hamilton T C. Increased platinum-DNA damage tolerance is associated with cisplatin resistance and cross-resistance to various chemotherapeutic agents in unrelated human ovarian cancer cell lines. Cancer Res., 57:850–6, 1997.
27. Harrap K R. Preclinical studies identifying carboplatin as a viable cisplatin alternative. Cancer Treat. Rev., 12:21–23, 1985.
28. Gore M, Fryatt I, Wiltshaw E, Dawson T, Robinson B, Calvert A. Cisplatin/carboplatin cross-resistance in ovarian cancer. Br. J. Cancer, 60:767–9, 1989.

29. Kelland L R, Murrer B A, Abel G, Giandomenico C M, Mistry P, and Harrap K R. Ammine/amine platinum(IV) dicarboxylates: a novel class of platinum complex exhibiting selective cytotoxicity to intrinsically cisplatin-resistant human carcinoma cell lines. Cancer Res., 52:822–8, 1992.
30. Anderson W K, Quagliato D A, Haugwitz R D, Narayanan V L, Wolpert-DeFilippes M K. Synthesis, physical properties and antitumor activity of tetraplatin and related tetrachloroplatinum(IV) stereoisomers of 1,2-diaminocyclohexane. Cancer Treat. Rep., 70:997–1002, 1986.
31. Misset J L, Kidani Y, Gastiaburu J, et al. Oxalatoplatinum (1-OHP): Experimental and clinical studies. In: Howell S B, editor. Platinum and other metal coordination complexes in cancer chemotherapy. Plenum Press, New York; 1991., p.369–375.
32. Schmidt W and Chaney S G. Role of carrier ligand in platinum resistance of human carcinoma cell lines. Cancer Res., 53:799–805, 1993.
33. Kelland L R. New platinum antitumor complexes. Clinical Reviews in Oncology/Hematology 1993; 15:191–219.
34. Fink D, Nebel S, Aebi S, Zheng H, Cenni B, Nehme A, et al. The role of DNA mismatch repair in platinum drug resistance. Cancer Res., 56:4881–6, 1996.

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A T10B45 cell line that is comprised of an expression vector comprising the coding sequence for enhanced fluorescent green protein operatively linked to the GADD153 promoter, wherein the promoter activity of said promoter is activated by cellular injury.

2. The cell line of claim 1, wherein said cellular injury is caused by agents selected from the group consisting of DNA cross-linking agents, DNA methylating agents, oxygen free radicals, DNA intercalator, UV radiation, gamma radiation, hypoxia, and platinum-containing chemotherapeutic drugs.

3. A method of screening a candidate compound for causing cellular injury comprising the steps of:

obtaining a culture of T10B45 cells;

contacting said culture of T10B45 cells with a candidate compound and contacting a second said culture of T10B45 cells with a control compound that does not cause cellular injury, wherein said T10B45 cells are comprised of an expression vector comprising the coding sequence of enhanced green fluorescent protein operatively linked to the GADD153 promoter and wherein expression of said enhanced fluorescent protein is induced in response to cellular injury; and measuring expression of said enhanced green fluorescent protein in both cultures, wherein an increased enhanced green fluorescent protein expression as a result of contact with said candidate compound as compared to contact with said control compound indicates that said candidate compound causes cellular injury.

4. The method of claim 3, wherein the expression of fluorescent protein is detected by flow cytometry.

5. A method of screening a candidate compound for causing cellular injury comprising the steps of:

obtaining a culture of T10B45 cells;

implanting said T10B45 cells into non-human mammals such that the T10B45 cells grow;

administering to a said mammal a candidate compound and administering to a second said mammal a control compound that does not cause cellular injury, wherein said T10B45 cells are comprised of an expression vector comprising the coding sequence of enhanced green fluorescent protein gene operatively linked to the GADD153 promoter and wherein expression of said enhanced green fluorescent protein is induced in response to cellular injury; and measuring expression of said enhanced green fluorescent protein in both mammals, wherein an increased enhanced fluorescent green protein expression as a result of contact with said candidate compound as compared to contact with said control compound indicates that said candidate compound causes cellular injury.

6. The method of claim 5, wherein the expression of green fluorescent protein is detected by flow cytometry.

7. A method of screening a library of candidate compounds for their relative potency in causing cellular injury comprising the steps of:

contacting a T10B45 cell line of claim 1 with a candidate compound from a library of candidate compounds and contacting a second of said T10B45 cell line with a control compound that does not cause cellular injury; and measuring expression of enhanced fluorescent green protein in both cell lines, wherein the level of increased enhanced fluorescent green protein expression as a result of contact with said candidate compound as compared to contact with said control compound is indicative of said candidate compound in causing cellular injury.

8. The method of claim 7, wherein the expression of green fluorescent protein is detected by flow cytometry.

* * * * *

UNITED STATES PATENT AND TRADEMARK OFFICE
CERTIFICATE OF CORRECTION

PATENT NO.    : 6,344,324 B2
DATED         : February 5, 2002
INVENTOR(S)   : Stephen B. Howell and Xinjian Lin It is certified that error appears in the above-identified patent and that said Letters Patent is hereby corrected as shown below:

Column 3,
Line 10, please delete the underscore.
Line 17, "hour" should read -- hr --.
Line 42, "And" should read -- and --.

Column 4,
Line 3, please replace the period after "nomenclature" with a comma.

Column 8,
Line 17, please insert a comma after "et al".
Line 24, please insert a comma after "et al".

Column 9,
Line 14, please delete the period after "strategy to".

Column 10,
Line 19, "CLONTECH" should read -- "Clontech" --.
Line 61, "hours" should read -- hrs --.

Column 11,
Line 7, "h" should read -- hr --.
Line 61, please insert a space before "and".

Column 12,
Line 13, "hour" should read -- hr --.
Line 15, "hour" should read -- hr --.
Line 16, "hours" should read -- hrs --.
Line 26, "hour" should read -- hr --.
Line 34, "hours" should read -- hrs --.
Line 47, "hour" should read -- hr --.
Line 61, "hour" should read -- hrs --.
Line 64, please insert a space before "and".
Line 67, "hour" should read -- hr --.

Column 13,
Line 2, please insert a space before "and".
Line 10, "hour" should read -- hr --.
Line 34, please insert a space before "the".
Line 43, "5- fluorouracil" should read -- 5-fluorouracil --.

Column 14,
Line 53, please insert a space before "or".

UNITED STATES PATENT AND TRADEMARK OFFICE
CERTIFICATE OF CORRECTION

PATENT NO. : 6,344,324 B2
DATED : February 5, 2002
INVENTOR(S) : Stephen B. Howell and Xinjian Lin It is certified that error appears in the above-identified patent and that said Letters Patent is hereby corrected as shown below:

Column 15,
Line 3, "3.8- fold" should read -- 3.8-fold --.
Line 32, please insert a space before "the".
Line 36, please delete the space before ">transplantin".

Column 17,
Line 45, "Bbiologist" should read -- Biologist --.
Line 46, please insert a comma after "A J Jr.".
Line 49, please insert a comma after "A J Jr.".
Line 49, please insert a comma after "Hollander".
Line 54, please insert a comma after "J Jr.".
Line 54, please insert a space between "O" and "W".
Line 62, please insert a comma after "A J Jr.".

Column 18,
Line 26, please insert the word -- and -- before "Kain".
Line 42, please insert the word -- and -- after "Spina A. M."

Column 19,
Line 17, please delete the second period after "1991".

Column 20,
Line 14, please insert the word -- said -- after the word "expression of".
Line 56, please insert the word -- said -- before the word "green".

Signed and Sealed this

Thirteenth Day of August, 2002

*Attest:*

JAMES E. ROGAN
*Director of the United States Patent and Trademark Office*

*Attesting Officer*